United States Patent
Yoshioka et al.

(10) Patent No.: US 12,116,700 B2
(45) Date of Patent: Oct. 15, 2024

(54) APPARATUS FOR COLLECTING BAGWORM SILK THREAD AND METHOD FOR PRODUCING LONG BAGWORM SILK THREAD

(71) Applicants: NATIONAL AGRICULTURE AND FOOD RESEARCH ORGANIZATION, Tsukuba (JP); KOWA COMPANY, LTD., Nagoya (JP)

(72) Inventors: Taiyo Yoshioka, Tsukuba (JP); Tsunenori Kameda, Tsukuba (JP); Takahiro Kitamura, Tsukuba (JP); Akimune Asanuma, Tsukuba (JP)

(73) Assignees: NATIONAL AGRICULTURE AND FOOD RESEARCH ORGANIZATION; KOWA COMPANY, LTD.

( * ) Notice: Subject to any disclaimer, the term of this patent is extended or adjusted under 35 U.S.C. 154(b) by 73 days.

(21) Appl. No.: 18/000,321

(22) PCT Filed: Jun. 1, 2021

(86) PCT No.: PCT/JP2021/020819
§ 371 (c)(1),
(2) Date: Dec. 30, 2022

(87) PCT Pub. No.: WO2021/246398
PCT Pub. Date: Dec. 9, 2021

(65) Prior Publication Data
US 2023/0220590 A1    Jul. 13, 2023

(30) Foreign Application Priority Data
Jun. 2, 2020   (JP) .................. 2020-096444

(51) Int. Cl.
  *D01B 7/04*    (2006.01)
  *D01F 11/02*    (2006.01)
(52) U.S. Cl.
  CPC ............... *D01B 7/04* (2013.01); *D01F 11/02* (2013.01); *D10B 2211/04* (2013.01)

(58) Field of Classification Search
  CPC ................................. D01B 7/00; D01B 7/04
  See application file for complete search history.

(56) References Cited

U.S. PATENT DOCUMENTS

| | | | | |
|---|---|---|---|---|
| 1,943,798 A | * | 1/1934 | Kowada | D01B 7/04 242/418.1 |
| 6,412,261 B1 | * | 7/2002 | Welshans | D01B 7/00 57/3 |

(Continued)

FOREIGN PATENT DOCUMENTS

| | | |
|---|---|---|
| JP | 2018197415 A | 12/2018 |
| WO | 2012165477 A1 | 12/2012 |

(Continued)

OTHER PUBLICATIONS

Kuwana et al., "High-Toughness Silk Produced by a Transgenic Silkworm Expressing Spider (*Araneus ventricosus*) Dragline Silk Protein", PLOS One, 2014, vol. 9, Issue 8, e105325, pp. 1-11.

(Continued)

*Primary Examiner* — Shaun R Hurley
(74) *Attorney, Agent, or Firm* — Lucas & Mercanti, LLP

(57) ABSTRACT

An object of the present invention is to develop: a method of efficiently producing a long bagworm silk thread without slack of reeling during collection while preventing a change in the spinning direction and the runaway of the bagworm from a rail, and alleviating a burden on the bagworm; and an apparatus for implementing the thread-producing method. Provided is an apparatus for producing a bagworm silk thread, including: a movable loop-shaped rail configured to move in the longitudinal direction and to be held by the legs of a bagworm; a fixator configured to fix the bagworm; and an adhesion controller configured to store an adhesion control solution for washing away or removing a gummy component from the bagworm silk thread spun on the movable loop-shaped rail, wherein the apparatus makes it possible to cumulate the bagworm silk thread spun on the movable loop-shaped rail.

7 Claims, 6 Drawing Sheets

(56) References Cited

U.S. PATENT DOCUMENTS

| | | | |
|---|---|---|---|
| 11,814,751 B2 * | 11/2023 | Kameda | D01B 7/00 |
| 2013/0281668 A1 * | 10/2013 | Vollrath | D01B 9/00 |
| | | | 119/270 |
| 2020/0157706 A1 | 5/2020 | Kameda et al. | |
| 2022/0022434 A1 | 1/2022 | Yoshioka et al. | |

FOREIGN PATENT DOCUMENTS

| | | |
|---|---|---|
| WO | 2019003364 A1 | 1/2019 |
| WO | 2020116503 A1 | 6/2020 |

OTHER PUBLICATIONS

Osaki, "Animals Teach Science on Natural Fibers:—Spider's Silks, Bagworm's Silks, and Collagen Fibers -", Journal of the Society of Fiber Science and Technology, 2002, vol. 58, No. 3, pp. 1-5, partial English translation 3 pages.

International Search Report for Corresponding International Application No. PCT/JP2021/020819, 2 pages, Aug. 17, 2021.

* cited by examiner (a)

(b)

(a)

(b)

(c)

(a)

(b)

(c)

(a)

(b)

APPARATUS FOR COLLECTING BAGWORM SILK THREAD AND METHOD FOR PRODUCING LONG BAGWORM SILK THREAD

CROSS-REFERENCE TO RELATED APPLICATIONS

This application is a 371 of PCT/JP2021/020819, filed Jun. 1, 2021, which claims the benefit of Japanese Patent Application No. 2020-096444, filed Jun. 2, 2020.

TECHNICAL FIELD

The present invention relates to a method of producing a long bagworm silk thread and an apparatus for producing the thread using the method.

BACKGROUND ART

The thread composed of an insect cocoon or a hair of mammal has been used as an animal fiber for a cloth and the like since long time ago. In particular, a silk thread from a silk moth (*Bombyx mori*) larva, namely a silkworm, which is herein often referred to as a "silkworm silk thread", has excellent properties for absorption and desorption of moisture, moisture retention, and heat retention, and also has a unique gloss and a smooth texture. Therefore, the silkworm silk thread is valuable and expensive natural material even today.

Recently, research is ongoing to search from nature for an animal fiber having properties comparable or superior to those of a silkworm silk thread, and such an animal fiber is expected to be utilized as a novel natural material. A good example of such an animal fiber is a thread from a spider (herein often referred to as a "spider thread") or a silk thread from a bagworm (herein often referred to as a "bagworm silk thread").

A spider thread has an elastic force several times greater than that of polystyrene, and besides, properties such as flexibility and elasticity. Silk from a silkworm in which a warp thread protein of such a spider is expressed is thus expected to be used as a special material for a medical material for suture and emergency ropes, protective clothes, or the like (Non-Patent Literature 1 and 2). However, many problems remain to be solved before practical use of the spider thread. First, mass-production of spider threads is not feasible because mass-rearing of spiders and production of a large amount of thread from spiders are difficult, which also results in a problem of high production cost. However, this problem is now being solved by using a recombinant silkworm or *Escherichia coli* producing a spider thread (Patent Literature 1 and Non-Patent Literature 1). However, a recombinant is allowed to be reared or cultured only in facilities with predetermined equipment, which actualizes a new problem, for example, with a large maintenance or management burden.

On the other hand, in recent years, a bagworm silk thread has been attracting attention as an animal fiber having mechanically excellent properties even better than a spider thread. For example, a silk thread from the bagworm *Eumeta minuscula* has a very high strength, as indicated by the elastic modulus value which is 3.5 times higher than that of a silkworm silk thread and 2.5 times higher than that of a spider thread from *Nephila clavata* (Non-Patent Literature 2). Additionally, a bagworm silk monofiber has a cross-sectional area nearly one-seventh as large as that of a silkworm silk monofiber, which allows production of fine, thin and light fabrics with a smooth texture. Moreover, a bagworm silk thread has a gloss and a shiny appearance comparable or superior to that of a silkworm silk thread. A bagworm, like a silkworm, is easy to mass-rear and to use to produce a thread by allowing the larva to spin, and thus, such a thread, unlike a spider thread, can be mass-produced. Additionally, a bagworm is more advantageous than a silkworm in the context of management. For example, since the silkworm feeds on only raw leaves of mulberry in principle, the region for rearing and season for rearing depend on the supply area of mulberry leaves and the season of mulberry leaf development. In contrast, the bagworm is euryphagous, the specificity for food leaves is low, and many species of the bagworm can feed on leaves of trees of various species. Accordingly, food leaves for the bagworm are easily available, and the bagworm can be reared in any region. Also, the bagworm of some species can feed on leaves of evergreen trees. Thus, differently from mulberries, which are deciduous trees, it is possible to supply food leaves all year round. Thus, the cost for rearing can significantly be reduced compared with that for rearing the silkworm. Additionally, bagworm silk threads can be directly obtained from wild-type bagworms. Therefore, production of recombinant bagworms and special maintenance and management equipment are not needed, differently from spider thread production. For the above-mentioned reasons, the bagworm silk thread is expected as a promising novel natural material.

However, there are some problems to be solved so that bagworm silk thread can be put to practical use. A largest problem is that it is difficult to obtain a long fiber of 1 m or more from a bagworm. In the case of a silkworm, a silkworm silk thread is collected from a cocoon. A cocoon is formed with a thread continuously spun by the larva during pupation, and thus, cocoon cooking of the cocoon completed, followed by reeling, makes it relatively easy to obtain a long fiber of tens of meters or more. In contrast, a bagworm pupates in its nest where the bagworm spends its life in the larval stage, and therefore spins no cocoon for pupation. Additionally, because a bagworm nest is naturally assembled by relatively short silk threads entangled with each other, no long fiber more than 1 m usually exists in the nest. Furthermore, by any existing technology, a thread can be spun only from a fiber in the innermost layer, which contains little gummy component adhering around a silk thread, and the silk thread obtained from the innermost layer is only less than 50 cm long. For the above-mentioned reasons, it has been almost impossible to obtain a meter-scale bagworm silk monofiber by the existing technology. Actually, no fabric interwoven with a bagworm silk thread has been known.

For practical application of the bagworm silk thread, another problem is that pieces of leaves and twigs and the like are inevitably attached on the surface of a bagworm nest. In cases where the bagworm silk thread is produced from a nest for the purpose of commercialization, these contaminants need to be completely removed. However, the removal operation requires enormous labor and cost, thus resulting in increased production cost. Additionally, complete removal of the contaminants is difficult with existing technologies, which has a problem of leading to loss of quality of a final product due to, for example, contamination with a minute amount of small leaves as well as light-brown staining of a silk thread with pigments from the contaminants.

For the above-mentioned reasons, it has been essential to develop a method of producing a pure and long bagworm silk thread without contaminant, for practical application of a bagworm silk thread as a novel material of biological origin.

Besides a nest-making thread (nest silk thread), a bagworm spins a foothold thread for preventing fall from a branch or a leaf, in such a manner that the thread is drawn in a zigzag pattern, and hooks its claws into the thread to migrate. The present inventors have discovered that this thread for migration (foothold silk thread) is mechanically better than a nest silk thread, and have tried to develop a technique by which a foothold silk thread in long size is spun by and collected from a bagworm. As a result, the inventors have succeeded in stably mass-producing a continuous pure bagworm silk thread as long as tens of meters or more, which has hitherto been considered impossible, and have filed a patent application (Patent Literature 2) based on such a method. This method utilizes the nature of a bagworm which continues to spontaneously spin a foothold silk thread along the rail having a specific width, by placing the bagworm on the rail. The method is epoch-making as a method of producing a long bagworm silk thread, but has actualized new problems concurrently. One of the problems is about the stamina of a bagworm. A bagworm spins a thread, holding a nest, and thus, needs the energy for supporting the nest in addition to the energy for spinning. Because of this, spinning for a long time in one thread-producing process creates an undue burden on a bagworm. Additionally, a bagworm placed on a rail spins a thread in a given direction of movement along the rail in principle, but the bagworm has a relatively high degree of freedom, and thus, the bagworm occasionally changes the direction of movement, or leaves the rail in some cases. Such a change in the direction of movement can cause the tangle and tear of the thread being collected. Furthermore, in bagworm silk threads layered on a loop-shaped rail, the cumulated silk threads are strongly cemented each other with a gummy component, and in some cases, this makes it difficult to collect the threads from the rail or to carry out degumming, that is, to remove the gummy component.

To solve the above-mentioned problems, the present inventors have made further studies, developed an apparatus configured to automate the processes from bagworm silk thread spinning through to collection, and filed a patent application (Patent Literature 3) based on the apparatus. With this apparatus, comprising a fixator configured to fix a bagworm with a nest in the apparatus, and a movable rail configured to move in the long axis direction makes it possible to release a bagworm from a burden of supporting a nest, and also keep the moving directionality of the bagworm constant. This makes it possible to produce a long bagworm silk thread stably, and simultaneously maintain the stamina of a bagworm. For this apparatus, use of a loop-shaped rail is sufficiently the most space-saving, and preferable in terms of production efficiency. However, circling the rail results in forming layers of bagworm silk threads on the rail. Forming such layers of bagworm silk threads causes the silk threads to adhere strongly to one another with a sericin-protein-like gummy component. Thus, collecting the bagworm silk threads involves not only a process of peeling the bagworm silk threads from the rail but also a process of peeling the mutually adhering bagworm silk threads from one another. However, the gummy component is very firm, and on the contrary, a bagworm silk thread is thinner than a silkworm silk thread, and thus, forcible peeling can lead to the tearing of the bagworm silk thread. To avoid such tearing, it is necessary to collect the bagworm silk threads in such a manner that the bagworm silk threads will not adhere to one another.

CITATION LIST

Patent Literature

Patent Literature 1: WO2012/165477
Patent Literature 2: JP2018-197415A
Patent Literature 3: JP2018-227669

Non-Patent Literature

Non-Patent Literature 1: Kuwana Y, et al., 2014, PLoS One, DOI: 10.1371/journal.pone.0105325
Non-Patent Literature 2: Shigeyosi Ohsaki, 2002, Sen'i Gakkaishi (Sen'i To Kogyo), 58: 74-78

SUMMARY OF INVENTION

Technical Problem

According to JP2018-227669, the above-mentioned problem of how to collect bagworm silk threads in such a manner that the bagworm silk threads will not adhere to one another is solved by using an apparatus comprising a peeling container and a collection device. A thread-producing apparatus disclosed in JP2018-227669 is configured such that a bagworm silk thread spun on a loop-shaped rail is immediately peeled from the rail via a peeling container, and that the bagworm silk thread peeled is collected on a collection device. This method allows the bagworm silk thread spun to be collected before circling on the loop-shaped rail, and thus, does not allow the bagworm silk threads to adhere to one another on the rail. However, a new problem has been actualized in that, when the bagworm silk thread peeled from the loop-shaped rail is collected on the collection device, the bagworm silk thread often raises a slack of reeling. The slack of reeling can cause the bagworm silk thread to be broken.

In view of this, a problem to be addressed by the present invention is to further improve that apparatus for producing a bagworm silk thread which is disclosed in JP2018-197415A, and to improve a newly actualized problem regarding the slack of reeling of a bagworm silk thread when collected.

Solution to Problem

The slack of reeling of the bagworm silk thread is arose because the collection device is rotated synchronously with the rotation of the loop-shaped rail, and the spinning action of the bagworm is a little zigzag on the rail, whereas the bagworm silk thread is linearly collected on the collection device when reeled up. To solve this new problem, the present inventors have adopted a method in which a bagworm silk thread spun on a loop-shaped rail is not peeled from a rail immediately, but the bagworm silk thread is allowed to spin during a given period of time, and then, the bagworm silk threads cumulated on the rail are collected. The slack of reeling of the bagworm silk threads does not arise by collecting the bagworm silk threads cumulated on the rail with tension applied from the collection device. However, as above-mentioned, this method still remains to have a problem of how to peel the bagworm silk threads from one another. In view of this, the present inventors have solved the problem by immediately treating the bagworm silk threads spun on the loop-shaped rail with an adhesion control solution to thereby control the adhesive force of the gummy component. This method enables the adhesive force of the gummy component to be reduced suitably. Accordingly, the bagworm silk threads adhere to one another enough to be cumulated, but do not adhere strongly. Thus, from a silk thread lump cumulated during collection, one bagworm silk thread can be easily withdrawn without being entangled and with such a weak force as not to tear the bagworm silk thread. This eliminates the necessity of the management and regulation work for the prevention of the slack of reeling and entanglement of the bagworm silk threads during collection, making it possible to further enhance the production efficiency for a long bagworm silk thread. The present invention is based on the above-mentioned development results and will provide the following items.

(1) An apparatus for producing a bagworm silk thread, comprising: a movable loop-shaped rail comprising an accumulator; a fixator configured to fix a bagworm; and an adhesion controller; wherein the movable loop-shaped rail has a width smaller than the maximum width between the right and left legs of the bagworm fixed with the fixator, and is configured to be held by the legs of the bagworm, wherein the accumulator is integrally placed on the movable loop-shaped rail, and configured such that the bagworm silk thread spun on the movable loop-shaped rail by the bagworm fixed with the fixator can be cumulated, wherein the fixator is placed at a position such that the bagworm fixed can hold the movable loop-shaped rail, and wherein the adhesion controller stores an adhesion control solution, and is configured such that the bagworm silk thread spun on the movable loop-shaped rail is brought in contact with the adhesion control solution.

(2) The apparatus for producing a bagworm silk thread according to (1), further comprising one or more peeling containers, wherein the peeling container is configured to store a peeling solution and/or vapor for peeling the bagworm silk thread from the accumulator, and placed at a position such that the whole or a part of the accumulator can be brought in contact with the peeling solution and/or the vapor in the peeling container.

(3) The apparatus for producing a bagworm silk thread according to (1) or (2), further comprising a collection device independent from the movable loop-shaped rail, wherein the collection device is configured to collect the bagworm silk thread from the accumulator.

(4) The apparatus for producing a bagworm silk thread according to any one of (1) to (3), wherein the movable loop-shaped rail is circular.

(5) The apparatus for producing a bagworm silk thread according to any one of (1) to (4), wherein the movable loop-shaped rail is an automatic rail.

(6) The apparatus for producing a bagworm silk thread according to any one of (3) to (5), wherein the collection device comprises, on the periphery thereof, a bobbin configured to reel the bagworm silk thread.

(7) A method of producing a long bagworm silk thread, comprising: a spinning process of making a bagworm hold a movable loop-shaped rail with its legs and continuously spin along the movable loop-shaped rail, wherein the movable loop-shaped rail has a width smaller than the maximum width between the right and left legs of the bagworm used for thread-production, and is configured such that the legs of the bagworm can hold the movable loop-shaped rail; a contacting process of bringing the bagworm silk thread on the movable loop-shape rail in contact with an adhesion control solution after the spinning process; a cumulating process of accumulating the bagworm silk thread after the contacting process; and a collecting process of collecting the cumulated bagworm silk thread after the cumulating process; wherein in the spinning process, the bagworm for use or a bagworm nest thereof is fixed at a position such that the legs of the bagworm can hold the movable loop-shaped rail, and wherein the movable loop-shaped rail is configured to be moved in the longitudinal direction automatically and/or by the movement of the bagworm.

(8) The production method according to (7), further comprising a second contacting process of bringing the bagworm silk thread cumulated on the rail after the cumulating process in contact with a peeling solution and/or vapor.

The present specification encompasses the contents disclosed in the specification and/or drawings of Japanese Patent Application No. 2020-096444, on which the priority of the present application is based.

Advantageous Effects of Invention

An apparatus for producing a bagworm silk thread according to the present invention makes it possible to automate the processes from the spinning of a long bagworm silk thread through to the collection of the thread, and to produce the thread stably.

A method of producing a bagworm silk thread according to the present invention enables a bagworm to spin only in a given direction without giving the bagworm a burden of supporting a nest.

A method of producing a bagworm silk thread according to the present invention makes it possible that bagworm silk threads are cumulated in a process of bringing the bagworm silk threads in contact with an adhesion control solution, and allowed to adhere to one another and bunch together by virtue of such a weak force as to make it easy to peel the bagworm silk thread. This makes it easy to handle the bagworm silk threads cumulated, and eliminates the necessity of regulation of the slack of reeling and entanglement of the bagworm silk threads during collection. Additionally, separating the spinning and the collection completely makes it possible to decrease the thread-production space required, compared with a conventional production apparatus.

BRIEF DESCRIPTION OF DRAWINGS

FIG. 1(a) shows the front view, and FIG. 1(b) depicts the top view.

FIGS. 3(a), 3(b), and 3(c) show a rail (0301) constituted by the periphery of a disc, a rail (0302) constituted by the rim of a wheel, and a rail (0303) constituted by a tubular inner wall face, respectively.

FIGS. 4(a), 4(b), and 4(c) show a structure constituted by a plurality of claw-shaped members for holding an object to be fixed, a tubular structure embedded an object to be fixed, and a structure for binding an object to be bonded to (or attached to, or seamed with) a support, respectively.

FIGS. 5(a) and 5(b) show a disc-shaped bobbin and a cylindrical bobbin, respectively. Both of them each show salient portions (0501) placed at the ends of the bobbin.

DESCRIPTION OF EMBODIMENTS

Figure 1:
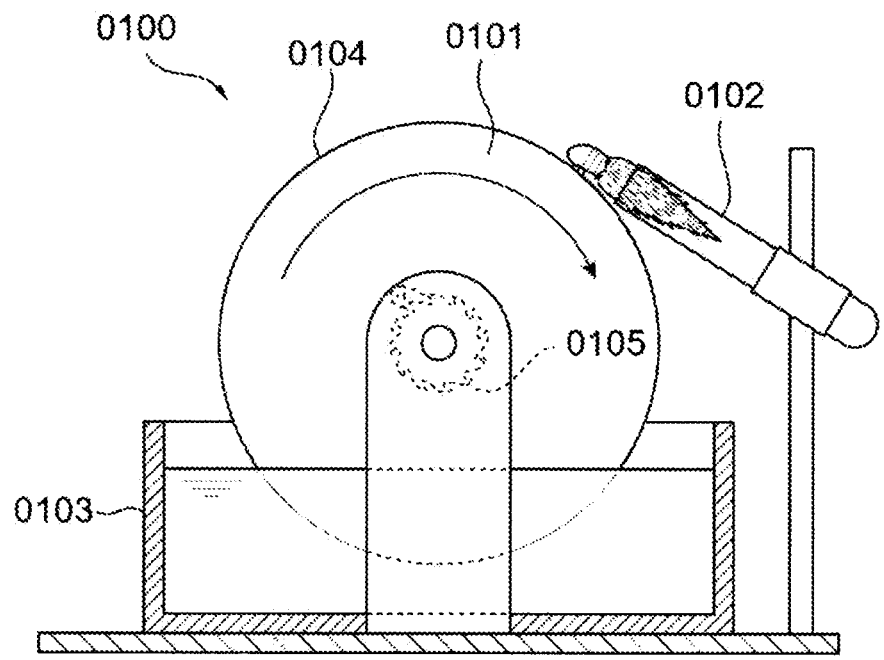
FIG. 1 shows a schematic of an apparatus for producing a bagworm silk thread according to the present invention.
Figure 1:
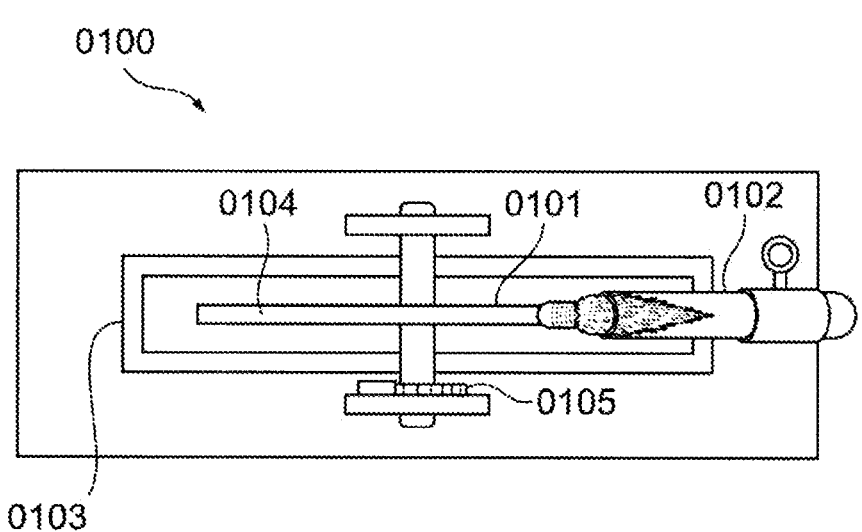

1. Apparatus for Producing Bagworm Silk Thread
1-1. Overview

A first aspect of the present invention is an apparatus for producing a bagworm silk thread. A thread-producing apparatus according to the present invention comprises a movable loop-shaped rail, a fixator, and an adhesion controller as essential constituents, and furthermore, the movable loop-shaped rail comprises an accumulator as an essential constituent. Additionally, the thread-producing apparatus comprises a peeling container and a collection device as optional constituents.

With a thread-producing apparatus according to the present invention, allowing a bagworm to maintain its stamina and keeping the moving directionality of the bagworm constant makes it possible to automate the production of a long bagworm silk thread. In addition, the thread-producing apparatus makes it possible to avoid the slack of reeling of the spun bagworm silk thread during collection, the breakage of the bagworm silk thread, or the entanglement of the threads during collection. This makes it possible that the production of a long bagworm silk thread is made efficient, that the production cost is decreased accordingly, and that the production is stable.

1-2. Definition

The following terms frequently used herein are defined as described below.

The term "bagworm" collectively refers to a moth larva belonging to the family Psychidae in the order Lepidoptera, as described above. Moths belonging to the family Psychidae are distributed worldwide and the larva (bagworm) of any species of the moth spends the whole larval stages living in a nest covered with natural materials, such as pieces of leaves and twigs, which are assembled by silk threads spun by the larva itself. The nest is a spindle-shaped, cylinder-shaped, or cone-shaped bag-like nest that can accommodate the whole body of a bagworm. A bagworm usually hides itself inside the nest and always carries the nest even during eating or moving and in principle, even pupates inside the nest. When the term "nest" is simply recited herein, it means a bagworm nest, unless specifically noted.

The species, instar, and gender of bagworms used herein are not limited, as long as the bagworm is a larva of a moth species belonging to the family Psychidae and the species makes a nest as described above. For example, the family Psychidae comprises the genera *Acanthopsyche, Anatolopsyche, Bacotia, Bambalina, Canephora, Chalioides, Dahlica, Diplodoma, Eumeta, Eumasia, Kozhantshikovia, Mahasena, Nipponopsyche, Paranarychia, Proutia, Psyche, Pteroma, Siederia, Striglocyrbasia, Taleporia, Theriodopteryx, Trigonodoma*, etc., and the bagworm used herein may be a species belonging to any genus. Specific examples of bagworm moth species comprise *Eumeta japonica, Eumeta minuscula*, and *Nipponopsyche fuscensis*. The instar of the larva may be any instar between the first instar and the last instar. However, a larger bagworm is preferable to obtain a thicker and longer bagworm silk thread. For example, among larvae of the same species, a larva in the last instar is more preferable, and a female larva is more preferable than a male larva because a female grows larger than a male. Furthermore, among the family Psychidae, a larger species is more preferable. Thus, *Eumeta japonica* and *Eumeta minuscula* are species that are preferable as the species of bagworms used in the present invention.

The term "silk thread" as used herein refers to a proteinous thread from an insect, which is spun by the insect in the larval or adult stage for the purpose of nest building, migration, anchoring, cocooning, prey capture, and the like. When the term "silk thread" is simply recited herein, it means a bagworm silk thread, unless specifically noted.

The term "bagworm silk thread" as used herein refers to a bagworm-derived silk thread. The "bagworm silk thread" as used herein encompasses a monofiber, spun fiber, and fiber assembly.

The term "monofiber" as used herein, which is also referred to as monofilament, is the smallest filament unit constituting a fiber component. The monofiber contains, as a main component, a fibroin-like protein constituting a silk thread. A bagworm silk thread in a natural state is spun as a bifilament in which two monofibers are joined together by a gummy component composed of a protein. This spun bifilament is referred to as a "spun fiber". The spun fiber is degummed, thus enabling the gummy component to be removed and affording a monofiber.

The term "fiber assembly" as used herein, which is also referred to as multifilament, refers to a fiber composed of a plurality of bundles of fibers. The fiber assembly refers to a so-called raw silk thread, and is composed of a plurality of monofibers in principle. Herein, however, the fiber assembly also encompasses a fiber assembly composed of a plurality of monofibers and spun fibers or a plurality of spun fibers. Though the term "fiber assembly" as used herein can encompass a fiber mixture composed of a mixture of a bagworm silk thread and another fiber such as a silkworm silk thread, the term is intended herein to mean a fiber assembly composed of a bagworm silk thread alone, unless specifically noted. The fiber assembly is twisted by a twisting process to become a stronger silk thread. However, the fiber assembly in this specification encompasses not only a twisted fiber assembly but also a non-twisted fiber assembly exhibiting a flexible and smooth texture.

The bagworm silk thread comprises a foothold silk thread and a nest silk thread. The "foothold silk thread" refers to a silk thread spun by a bagworm spins in advance of migration and a function as a foothold for preventing fall from a branch, leaf, or the like during migration. A bagworm usually uses a foothold silk thread as a foothold and hooks its claws onto the foothold silk thread to move in the direction of migration. A foothold silk thread is spun by a bagworm swinging its head right and left, and every time the head is swung, the silk thread is fixed to twigs and leaves as a base with the above-mentioned gummy component, and thus, is usually spun in a zigzag pattern. This structure makes it easier for the bagworm to hook the right and left legs onto the foothold silk thread, and causes the load on the silk thread fixation portion or the silk thread itself to be distributed right and left. On the other hand, the "nest silk thread" refers to a silk thread forming a nest, which is spun to assemble pieces of leaves and twigs or to make an inner wall of a nest so that its accommodation space can become a comfortable environment. In principle, a foothold silk thread is thicker and also mechanically stronger than a nest silk thread.

As used herein, the term "long" refers to a length longer than the normal length in the art. As used herein, the term "long" especially refers to being longer than the length of a spun silk threads (a length of less than 1 m) obtainable from a bagworm using conventional technology. Specifically, the term "long" refers to 1 m or more, preferably 1.5 m or more or 2 m or more, more preferably 3 m or more, 4 m or more, 5 m or more, 6 m or more, 7 m or more, 8 m or more, 9 m or more, or 10 m or more. The upper limit of the length is not particularly limited, but corresponds to the length of a silk thread which a bagworm can continuously spin. For example, the length is 1.5 km or less, 1 km or less, 900 m or less, 800 m or less, 700 m or less, 600 m or less, 500 m or less, 400 m or less, 300 m or less, 200 m or less, or 100 m or less. The length of a spun fiber of a bagworm silk thread is also the length of a monofiber constituting the fiber, and corresponds to the length of the thread continuously spun by a bagworm. Therefore, a longer bagworm silk thread can be obtained if it is possible to make a bagworm spin a thread continuously.

As used herein, the term "thread-producing (or producing a thread)" refers to make a bagworm spin a silk thread for the purpose of obtaining a bagworm silk thread. For a thread-producing apparatus according to the present invention, however, "thread-producing" can comprise not only spinning but also collecting the spun silk thread. In the present specification, a bagworm silk thread to be produced is a foothold silk thread.

The term "leg" as used herein refers to an entire leg or a part of a leg of a bagworm. Legs called thoracic legs extend from the thorax of a bagworm. The thoracic legs consist of three legs (front, middle, and rear legs) located on each side, which means three pairs of right and left legs, with a total of six legs.

The term "hold" generally refers to hooking and holding, but herein refers to that a bagworm holds its legs on a rail to move on the rail. A bagworm usually uses its legs to hold a twig or a leaf to support the whole or a part of the weights of itself and a nest. That is, although the meaning of "hold" comprises preventing a bagworm itself and its nest from falling, in the present invention, a bagworm is fixed and does not need supporting its own weight. Accordingly, the meaning of "hold" as used herein does not encompass supporting a bagworm's own weight, in principle. In this regard, a bagworm is free to hold or release an object, and does not mean that the legs which have once caught an object become fixed at the holding position. A bagworm uses its legs to repeat holding and releasing a rail so that the bagworm can freely move on a rail.

1-3. Constitution

FIG. 1 is a schematic diagram of a thread-producing apparatus according to the present invention. As shown in this drawing, a thread-producing apparatus according to the present invention (0100) comprises a movable loop-shaped rail (0101), a fixator (0102), and an adhesion controller (0103) that are in a spinning unit. Additionally, the thread-producing apparatus according to the present invention comprises a peeling container and a collection device that are in a collection unit (not shown). In the thread-producing apparatus according to the present invention, each constituent in the spinning unit is an essential constituent, and each constituent in the collection unit is an optional constituent. Each of the constituents will be described below.

1-3-1. Movable Loop-Shaped Rail

A "movable loop-shaped rail" (0101) is a loop-shaped rail configured to move in the longitudinal direction, and is comprised as an essential constituent in the spinning unit for spinning a bagworm silk thread in a thread-producing apparatus according to the present invention. The movable loop-shaped rail comprises an accumulator (0104) as an essential constituent, and can also comprise a ratchet (0105), if necessary.

(1) Constitution of Rail

A "rail" as used herein refers to a path with a linear structure on which a bagworm moves. The "linear structure" as used herein refers to a single-rail structure with a same or substantially same width, whose cross sectional shape is not limited to any particular shape, but comprises circular shapes, approximately circular shapes (comprising oval shapes), polygonal shapes (comprising square and approximately square shapes), and combinations thereof.

The width of a rail is made less than the maximum width between the extended legs of a bagworm used for a thread-producing apparatus according to the present invention. The "width of a rail" as used herein refers to the length of a moiety of the rail, which is directly related to holding legs of a bagworm on the rail when the legs of the bagworm hold the rail. This length generally corresponds to the transverse (short axis) length of the rail. The maximum width of the rail is less than the maximum width between the extended legs of a bagworm used for the thread-producing apparatus according to the present invention. On the other hand, the minimum width of the rail is not limited to any particular length, as long as a bagworm can hold the legs on the rail. For example, the rail may be on the edge of a thin metal plate with a thickness of around 0.5 mm. In the rail shown in FIG. 2A, the cross-sectional diameter ($\varphi$) corresponds to the width of the rail.

Figure 2:
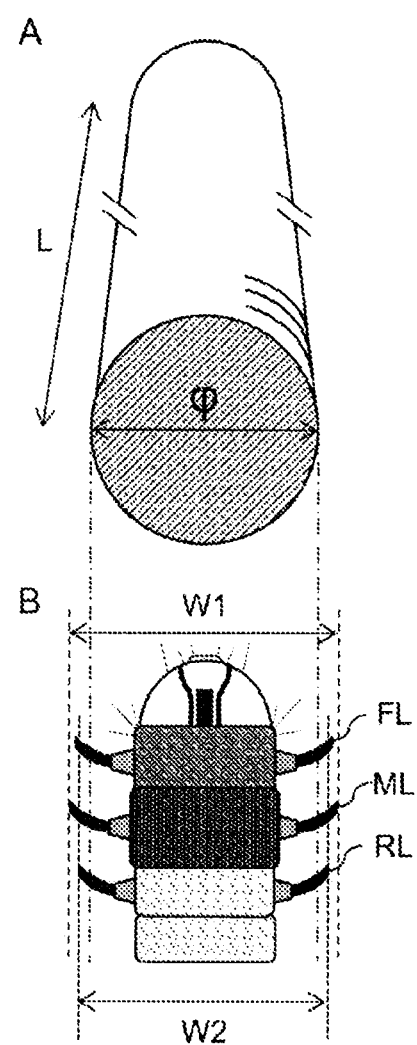
FIG. 2A shows a schematic of a rail in an apparatus for producing a bagworm silk thread according to the present invention. This figure shows a rail having a circular cross section. In the figure, L and φ represent the length of the rail in the longitudinal axis and the cross-sectional diameter of the rail respectively. In the rail, φ corresponds to the width of the rail.
FIG. 2B shows a dorsal view of the head and thorax of a bagworm spreading out the legs to the right and left at the maximum width. In the figure, FL, ML, and RL represent the front legs, middle legs, and rear legs, respectively. W1 and W2 represent the maximum width between the right and left legs when the bagworm spreads out its legs, for middle legs and rear legs, respectively.

The "maximum width between the extended legs of a bagworm" as used herein refers to the width (W1 or W2) between the right and left legs of the bagworm, which are extended right and left as much as possible, as shown in FIG. 2B. A bagworm has three pairs of right and left legs (front, middle, and rear legs), and the maximum width between the extended legs preferably represents either of the maximum widths except for the longest (maximum) width between the extended legs, namely the second longest width or the shortest width between the extended legs. The maximum width more preferably represents the shortest (minimum) width between the extended legs. In FIG. 2B, the maximum width (W1) between the extended middle legs (ML) is the longest, and the maximum width (W2) between the extended rear legs (RL) is the shortest among the three pairs of legs. Therefore, when the width of a rail is determined, the maximum width between the extended front legs (FL) or between the extended rear legs (RL), particularly the maximum width between the extended rear legs (RL), W2 is preferable as the maximum width between the extended legs of a bagworm. The maximum width between the extended legs varies depending on the species, male and female, and instar of larvae, but generally falls within a specific range if the bagworms are the same species of nearly the same instar. For example, in *Eumeta japonica*, the maximum width between the extended legs of young instar bagworms (around the first to third instar) ranges from 2 mm to 4 mm or from 3 mm to 5 mm. That of the middle instar larva (around the fourth to fifth instar), ranges from 3 mm to 7 mm or from 4 mm to 8 mm. That of the penultimate instar larva or last instar larva ranges from 4 mm to 9 mm, from 5 mm to 10 mm, or from 6 mm to 12 mm. In *Eumeta minuscula*, the maximum width between the extended legs of young instar larva (around the first to third instar) ranges from 1.5 mm to 3.5 mm. That of the middle instar larva ranges from 2.5 mm to 6 mm or from 3 mm to 7 mm. That of the penultimate instar larva or last instar larva ranges from 3.5 mm to 8 mm, from 4 mm to 9 mm, or from 5 mm to 10 mm. Thus, the width of the rail should be changed as appropriate according to the species, instar, and male and female of a bagworm for use. In each larval instar, the width of the rail is preferably less than the shortest (minimum) among the maximum widths between the extended legs of a bagworm of the species used, in terms of holding legs as described below.

The rail is configured such that the legs of a bagworm can hold a rail. The expression "the legs can hold" refers to having a structure such that the legs of a bagworm can hold a rail. Any of the legs may hold a rail. Examples of such a manner comprise: a manner in which at least a pair of legs, one each from the right and left sides, among the six legs, that is, the three pairs of legs, of a bagworm hold a rail between the legs; and a manner in which two or three legs on either the right or left side of a bagworm hold a rail in such a manner that the rail runs beneath the thorax. If the legs of a bagworm can hold a rail, the bagworm can move along the rail, spinning a foothold silk thread on the rail.

A rail in an apparatus for producing a bagworm silk thread according to the present invention is a loop-shaped rail. The "loop-shaped rail" refers to a rail having no end and having a loop shape as a whole. When the term "rail" is simply recited herein, it means a "loop-shaped rail" or the below-mentioned "movable loop-shaped rail", unless specifically noted. The loop-shaped rail has no end, and thus, makes it possible to collect a long silk thread as long as a bagworm continues to circle on the rail. The loop-shaped rail may be in the form of a closed loop or an open loop. The loop-shaped rail is preferably a closed loop. In the case of the open loop, a gap in the open loop portion should have a width such that a bagworm for use can go across the gap. Such a gap may exist at a plurality of positions in an open loop-shaped rail. Additionally, examples of the entire shape of a loop-shaped rail comprise circular shapes, approximately circular shapes, square shapes, approximately square shapes, polygonal shapes, indefinite shapes, and combinations thereof. A circular loop-shaped rail with a circular shape, or an oval loop-shaped rail with an approximately circular shape is preferable.

Figure 3:
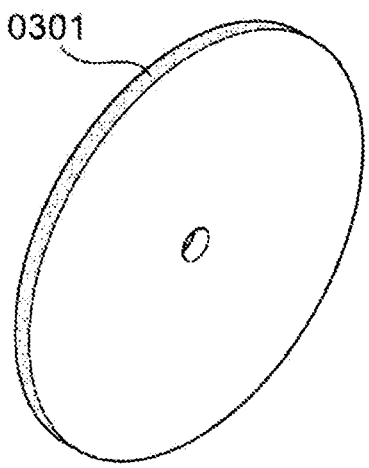
FIG. 3 shows a specific example of a rail in an apparatus for producing a bagworm silk thread according to the present invention.
Figure 3:
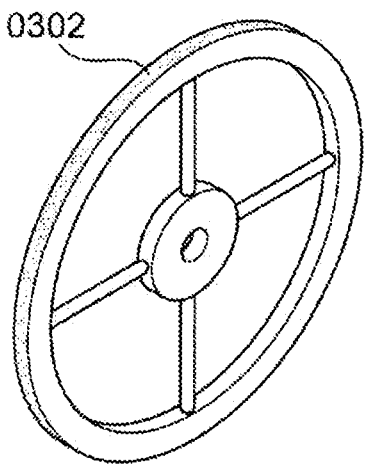
Figure 3:
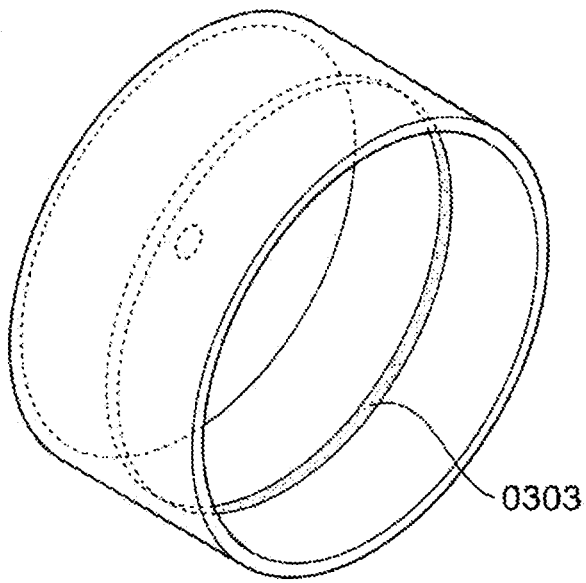

Specific examples of circular loop-shaped rails comprise a rail (0301) constituted by the periphery of a disc shown in FIG. 3(*a*), a rail (0302) constituted by the rim of a wheel shown in FIG. 3(*b*), and a rail (0303) constituted by a tubular inner wall face shown in FIG. 3(*c*).

A rail constituted by the periphery of a disc (0301) refers to a rail constituted by the periphery of a circular plate-like member. In this case, the thickness of the disc corresponds to the width of the rail. The diameter Φ of the disc may be in, but is not limited to, the range of from 5 cm to 50 cm, from 10 cm to 30 cm, from 15 cm to 25 cm, or from 17 cm to 20 cm.

A rail constituted by the rim of a wheel (0302) refers to a rail constituted by circularizing a rod-like member, such as a wire. In this case, the diameter or transverse width of the rod-like member corresponds to the width of the rail. As with the diameter of the above-mentioned disc, the diameter Φ of the wheel may be in, but is not limited to, the range of from 5 cm to 50 cm, from 10 cm to 30 cm, from 15 cm to 25 cm, or from 17 cm to 20 cm.

A rail constituted by a tubular inner wall face (0303) refers to a rail configured by a part of a tubular inner wall face. This part is constituted as a loop-shaped salient along the tubular internal circumferential face, and has a structure in which the transverse width of the salient corresponds to the width of the rail. The diameter Φ of the tubular internal circumference may be in, but is not limited to, the range of from 10 cm to 60 cm, from 15 cm to 50 cm, from 20 cm to 40 cm, or from 25 cm to 30 cm.

The material of the rail is not limited. For example, metals, ceramics (comprising enamel), glass, stones, resins (comprising synthetic and natural resins), wood materials (comprising branch, bine, bamboo, and the like), fibers, bones and fang, and combinations thereof can be used. The material is preferably invulnerable to the biting attack of a bagworm. For example, metals, ceramics, glass, stones, and the like are preferable. Additionally, a portion of a rail to which a bagworm silk thread adheres is preferably made from a material with a smooth surface to facilitate collection of a bagworm silk thread spun. The "material with a smooth surface" as used herein refers to a material processable to form a smooth surface, such as metals, glass, and plastics. Additionally, any material coated with a paint or the like to obtain a smooth surface is encompassed in the material with a smooth surface, even if the original material is difficult to polish for the formation of a smooth surface, such as wood materials and fibers. When the rail is the periphery of a plate-like member, the plate-like member and the periphery may be made from the same material or from different materials.

The thread-producing apparatus can comprise a plurality of rails. The conditions such as the shapes and materials of the rails may be the same or be different, or may be a combination thereof. Examples comprise rails configured by the peripheries of a plurality of coaxial discs placed in parallel.

A rail in a thread-producing apparatus according to the present invention may have a slope relative to a horizontal plane. The slope angle is not limited to any value. For example, when the rail is configured by the periphery of a disc, and if the planar portion of the disc member as a base is placed horizontally, the slope angle of the rail is 0 degrees. On the other hand, when the planar portion of the disc member is placed vertically, the rail can encompass every slope angle.

(2) Constitution of Movable Loop-Shaped Rail

A "movable loop-shaped rail" is configured such that the loop-shaped rail moves in the longitudinal direction. The "longitudinal direction" as used herein refers to the direction along the long axis of the rail. This means that the loop-shaped rail is configured such that the rail is rotated. For example, in cases where the loop-shaped rail is a circular loop-shaped rail constituted by the periphery of a disc, the whole disc member has a rotatable structure.

Without limitation, the movable loop-shaped rail is configured to rotate so as to synchronize with the movement of a bagworm spinning in the direction of movement on the rail. Accordingly, a force required for the initial motion of the rail is preferably equal to or less than a movement impelling force generated when a bagworm moves on the rail. Examples of powers for driving a rail comprise a movement impelling force of a bagworm, electrical power, and the like.

A "movement impelling force of a bagworm" is an impelling force generated by a bagworm moving along the rail. In a thread-producing apparatus according to the present invention, a bagworm is fixed by the below-mentioned fixator. Accordingly, even if the bagworm moves, spinning on the rail, it substantially cannot advance in the direction of movement. The movement impelling force generated by the movement of the bagworm can drive the rail as a force acting in the direction opposite to the direction of movement of the bagworm. In the present specification, this force is referred to as the movement impelling force of a bagworm.

On the other hand, the rail can be configured to be automatically driven by an electrical power via a motor, a gear, and the like. The direction of movement of this automatic rail is opposite to the direction of movement of a bagworm. Additionally, the moving speed of the rail is preferably approximately equal to or less than the moving speed of a bagworm. The specific moving speed of a bagworm varies depending on the kind, instar, individual size, and the like of the bagworm, and is usually in the range of from 3 m/hr to 15 m/hr, or in the highest range of from 17 m/hr to 22 m/hr. Accordingly, the automatic rail may be moved at a moving speed (v) equal to or less than these speeds. For example, the moving speed may be as follows: $0$ m/hr$<$v$\leq$22 m/hr, $0$ m/hr$<$v$\leq$20 m/hr, $0$ m/hr$<$v$\leq$17 m/hr, $0$ m/hr$<$v$\leq$15 m/hr, $0$ m/hr$<$v$\leq$12 m/hr, $0$ m/hr$<$v$\leq$10 m/hr, $0$ m/hr$<$v$\leq$8 m/hr, $0$ m/hr$<$v$\leq$5 m/hr, $0$ m/hr$<$v$\leq$4 m/hr, or $0$ m/hr$<$v$\leq$3 m/hr. In cases of using an automatic rail, the movement impelling force of a bagworm concurrently acts on the rail during spinning. That is, the automatic rail is a mechanism for assisting a bagworm in moving. In this case, since a driving force of the automatic rail is added, a burden on a bagworm moving can be significantly alleviated.

In this regard, the movable loop-shaped rail is configured to have the capability to be mounted in and removed from the thread-producing apparatus according to the present invention. This capability to be mounted and removed is convenient to associate the movable loop-shaped rail with a peeling container and/or a collection device placed at different positions in the thread-producing apparatus, in cases where the bagworm silk threads cumulated in an accumulator on the below-mentioned movable loop-shaped rail are left cumulated, or when the bagworm silk threads are collected.

The movable loop-shaped rail comprises an "accumulator" (0104) as an essential constituent, and can also comprise a ratchet (0105) as an optional constituent. Each constituent will be described below.

(a) Accumulator

The "accumulator" (0104) is integrally placed on the movable loop-shaped rail, and configured to cumulate bagworm silk threads spun.

As used herein, the term "integral" refers to being one indivisible piece. That is, the spinning face of the rail constitutes the accumulator, and the accumulator is configured to retain layers of bagworm silk threads on the spinning face of the rail. As used herein, the word "cumulate" means that a bagworm silk thread is spun on the spinning face a plurality of times. The cumulation of bagworm silk threads is achieved by allowing a bagworm fixed with the fixator to spin on the movable loop-shaped rail during more than one rotation (one round). The bagworm silk threads on the accumulator do not necessarily need to be in contact with one another. However, the bagworm silk threads cumulated on the accumulator will soon come in contact with one another as the number of times when the bagworm silk thread spun on the rail circles increases. Furthermore, the bagworm silk thread results in layers. In cases where a plurality of bagworm silk threads spun on a loop-shaped rail come in contact with one another in a conventional method, the gummy component causes the bagworm silk threads to adhere strongly to one another, and thus, it is difficult to peel the bagworm silk threads without tear or damage. Because of this, the adhesion between the bagworm silk threads spun on the loop-shaped rail is avoided by collecting the bagworm silk threads before the bagworm silk threads spun on the rail are circled. In a thread-producing apparatus according to the present invention, however, the below-mentioned adhesion controller makes it possible to easily separate the bagworm silk threads even in cases where the bagworm silk threads come in contact with one another on the accumulator, and layered. Accordingly, the bagworm silk threads can be cumulated without being collected until the bagworm completes spinning.

(b) Ratchet

The movable loop-shaped rail may comprise a "ratchet" (0105) as an optional constituent. The "ratchet" is a portion for restricting the direction of movement to one direction. Without limitation, the ratchet is usually constituted by: a gear with teeth slanted in a given direction; and a pallet placed so as to lock the teeth. The structure is such that, when the gear rotates reversely, the pallet locks the teeth of the gear, thereby the gear can be rotated only in the given direction.

In a thread-producing apparatus according to the present invention, by synchronizing the movement of the movable loop-shaped rail with that of the gear each other, the movable loop-shaped rail can move only in one direction. For example, when the movable loop-shaped rail is constituted by the periphery of a disc, making the disc and the gear be coaxial enables the disc to be rotated only in the direction of rotation allowed by the ratchet. Comprising this portion makes it possible that the movable loop-shaped rail is not moved even though a bagworm holding the rail moves backward, thereby the spinning direction is not changed and always kept in a given direction.

The ratchet can have a release function, if necessary.

1-3-2. Fixator

A "fixator" (0102) is a holder for fixing a bagworm to be used for thread-producing. In a thread-producing apparatus according to the present invention, the fixator is an essential constituent that, together with the above-mentioned movable loop-shaped rail and the below-mentioned adhesion controller, constitutes the spinning unit.

The fixator is configured to fix a bagworm at a predetermined position in a thread-producing apparatus according to the present invention. The fixator has a function for restricting the free movement of a bagworm in a thread-producing apparatus according to the present invention, and allowing the bagworm to spin in a given moving direction on the rail. The fixator makes it possible that a change in the direction of movement of a bagworm and the runaway of the bagworm from the rail during spinning are restricted.

Figure 4:
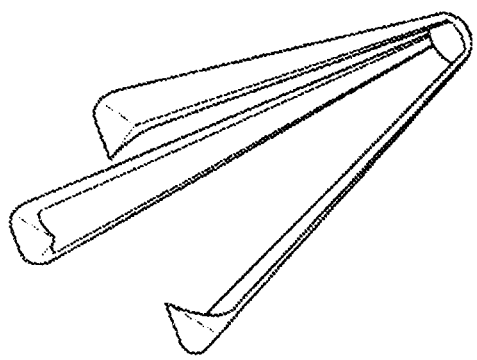
FIG. 4 shows a schematic of a fixator in an apparatus for producing a bagworm silk thread according to the present invention.
Figure 4:
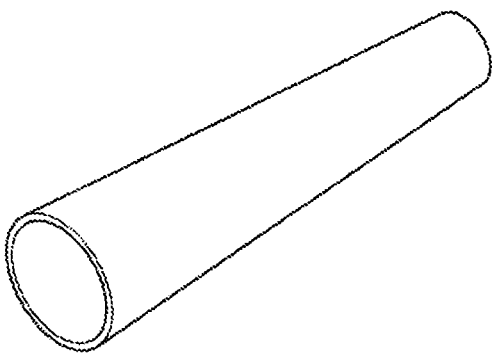
Figure 4:
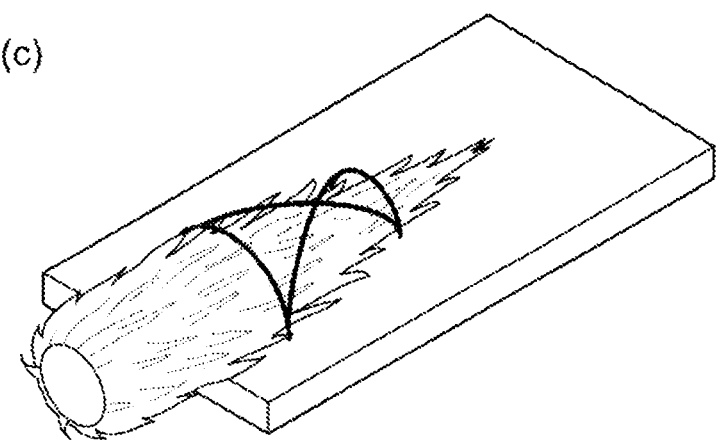

The method for fixing of a bagworm is not limited. Examples of the fixing method comprise: a structure constituted by a plurality of claw-shaped members for holding an object to be fixed as shown in FIG. 4(*a*); a tubular structure into which an object to be fixed is to be fitted as shown in FIG. 4(*b*); and a structure in which an object to be fixed is to be bonded to (or attached to or seamed with) a support as shown in FIG. 4(*c*). However, any structure can be used, as long as the structure can fix an object. A fixation adjustment portion for finely adjusting a fixing force may be comprised so that a bagworm as an object to be fixed is subjected to no excessive burden or pressure when the bagworm is fixed.

The object to be fixed is either the bagworm nest (on the premise that the bagworm exists inside the nest) or a bagworm itself. The object is preferably the nest. This is because a bagworm separated from the nest falls under excessive stress by continuing a naked state, posing the possibility of having an influence on the amount of spinning and the efficiency of spinning.

In a thread-producing apparatus according to the present invention, the fixator is placed at a position at which the fixed bagworm can hold the above-mentioned movable loop-shaped rail. The fixator may comprise a position adjustment portion which makes the position of a fixed bagworm adjust right and left and backward and forward to place the fixed bagworm at the position at which the legs of the bagworm can just hold the rail.

1-3-3. Adhesion Controller

The "adhesion controller" (0103) is a container in which a bagworm silk thread spun on the movable loop-shaped rail is brought in contact with an adhesion control solution. In a thread-producing apparatus according to the present invention, the adhesion controller is an essential constituent that, together with the movable loop-shaped rail and the fixator, constitutes the spinning unit. The adhesion controller has a function by which a part of the gummy component attached to the surface of the bagworm silk thread spun on the rail is washed away or removed with the adhesion control solution contained in the adhesion controller, reducing the adhesion effect of the gummy component, so that the adhesive force of the bagworm silk thread to the accumulator on the rail is controlled. With the remaining gummy component, the adhesiveness remains, but, the adhesive force is reduced, thus making it possible that the bagworm silk thread is peeled easily with such a degree of tension as not to cause breakage, even in cases where the bagworm silk threads come in contact with one another on the accumulator. Additionally, allowing the gummy component to remain makes it possible to manage the bagworm silk threads in the form of a silk thread bundle cohered with a suitable adhesive force without causing the bagworm silk threads to be entangled with one another.

The adhesion controller is not limited to any specific configuration as long as the adhesion controller can come in contact with the bagworm silk threads on the rail. Examples of a configuration which allows the bagworm silk threads to be brought in contact with the adhesion control solution comprise a configuration which allows the adhesion control solution to be, for example, sprayed, scattered, applied, dripped, used for immersion, or exuded. Specifically, for example, such a configuration needs only to be as follows; a part of the rail is immersed in the adhesion control solution in the adhesion controller; the adhesion control solution in the adhesion controller is dripped onto a part of the rail; the adhesion control solution is sprayed or scattered from the adhesion controller onto a part of the rail; or the adhesion control solution in the adhesion controller integrated with the rail is exuded through a part of the exudation grooves and/or exudation holes made in the rail. Alternatively, such configurations may be combined.

The adhesion controller is not limited to any shape. Examples of the shape comprise: the shape of a storage tank; the shape of a container having a dripping hole or an injection hole through which the adhesion control solution in the container can be dripped or injected onto a part of the rail; the shape of a tube or a disc having one or more exudation grooves or exudation holes opened to the flow path and the rail in the inside or lower portion of the rail; and the like. In cases where the adhesion controller has an exudation groove or an exudation hole, the exudation groove is not limited to any particular shape. The shape is, for example, a slit, wavy line, dashed line, or the like. Additionally, the exudation hole is not limited to any particular shape. For example, the shape may be any one of a circular, oval, triangular, square, approximately square, polygonal (for example, hexagonal), or indefinite shape. The width of the exudation groove and the size of the exudation hole are not limited. If the width of the exudation groove and the diameter of the exudation hole are too large, the adhesion controller is not enabled to achieve the original function as a place where a bagworm silk thread is spun. Thus, the width of the exudation groove and the diameter of the exudation hole are preferably smaller to a degree to which the adhesion control solution does not cause clogging. In this regard, the adhesion controller is desirably placed at a position at which the adhesion control solution is not in direct contact with the bagworm.

A material of the adhesion controller is not limited, as long as the rail or the adhesion controller or the inner wall thereof is neither dissolved, corroded, nor modified by the adhesion control solution. The material needs only to be determined as appropriate depending on the kind of an adhesion control solution to be stored. For example, in cases where the adhesion control solution is composed of an aqueous solution containing a surfactant, the adhesion controller is preferably made of plastic, ceramic (enamel), glass, or the like.

The adhesion controller can also comprise a supply port for supplying an adhesion control solution into the controller and/or a discharge port for discharging an adhesion control solution out of the controller.

A thread-producing apparatus according to the present invention may comprise one or more adhesion controllers. In cases where the thread-producing apparatus has a plurality of adhesion controllers, the shapes and sizes of the adhesion controllers may be the same or different, or may be a combination thereof. Additionally, in cases where the thread-producing apparatus has a plurality of adhesion controllers, the conditions such as the kind and volume of the adhesion control solution stored in each adhesion controller can be independently selected for each adhesion controller.

The "adhesion control solution" refers to a solution that is used to wash away or remove, from a bagworm silk thread, a part of a water-soluble gummy component (sericin-like protein) spun together with a fiber component (fibroin-like protein) and existing around the fiber component in the bagworm silk thread, and thus, makes it possible to control the adhesive force of the bagworm silk thread.

The adhesion control solution is not a liquid that completely removes the above-mentioned water-soluble gummy component, and thus, a part of the gummy component remains on the surface of the bagworm silk thread. The bagworm silk thread treated with the adhesion control solution loses a strong adhesive force owing to the decrease in the amount of the gummy component, but still has an adhesive force remaining a little. Because of this, the bagworm silk threads cumulated on the accumulator adhere to one another with a weak adhesive force, and are layered without falling apart. The bagworm silk threads layered are fixed in the form of a loop-shaped bundle (bagworm silk thread bundle). Thus, the subsequent handling is made easy, and the bagworm silk threads constituting the bundle will not be entangled among one another. On the other hand, the adhesive force between the bagworm silk threads in the above-mentioned bagworm silk thread bundle is weak, and thus, withdrawing a bagworm silk thread by pulling an end thereof makes it possible to withdraw the bagworm silk thread with such a degree of tension as not to cause tear and without slackly reeling the bagworm silk thread during collection.

The adhesion control solution makes it possible to control adhesion and peeling between the bagworm silk thread and the rail or between the bagworm silk threads. The adhesion control solution desirably has the property of causing no chemical and/or physical damage or being less likely to cause such damage to a bagworm silk thread.

The adhesion control solution is not limited, as long as the liquid has a function for washing away or removing the gummy component as above-mentioned. However, a liquid having a strong force for washing away or removing the gummy component, such as a degumming solution, completely removes the gummy component when brought in contact with the surface of the bagworm silk thread several times, and thus, is not preferable. The adhesion control solution may be water or an aqueous solution, and is particularly preferably a surfactant solution.

A "surfactant solution" refers to a solution of a surfactant dissolved in a preferable solvent. Examples of solvents comprise water (comprising distilled water, sterile water, and deionized water), physiological saline, and phosphate buffers. Water is preferable. The concentration of a surfactant in a solution may be, but is not limited to, 0.01% to 10%, 0.05% to 5%, 0.1% to 2%, or 0.5% to 1% in terms of % by volume.

A surfactant to be used for the surfactant solution is not limited. For example, the surfactant may be any of the following: nonionic surfactants such as Triton X-100, Triton X-114, NP-40, Brij-35, Brij-58, Tween-20, Tween-80, octyl-β-glucoside, and OTG; high molecular weight nonionic surfactants such as a copolymer of PEG and PPG; anionic surfactants such as SDS; zwitterionic surfactants such as CHAPS and CHAPSO; and combinations thereof.

In this regard, in cases where two or more adhesion controllers are placed on one rail, the same or different adhesion control solution may be stored in each adhesion controller.

1-3-4. Peeling Container

A "peeling container" is a container which can store a peeling solution and/or vapor. In a thread-producing apparatus according to the present invention, the peeling container is an optional constituent that, together with the below-mentioned collection device, constitutes the collection unit. In a thread-producing apparatus according to the present invention, the peeling container is configured such that the peeling solution and/or vapor encompassed in the peeling container come(s) in contact with all or a part of bagworm silk threads cumulated on the accumulator on the movable loop-shaped rail.

The basic constitution of the peeling container follows that of the adhesion controller. However, the adhesion controller and the peeling container differ in that the adhesion controller as a part of the spinning unit treats a bagworm silk thread that is being spun, whereas the peeling container as a part of the collection unit treats the bagworm silk threads spun and cumulated on the accumulator. The peeling container is an optional constituent, and has a function auxiliary to the adhesion controller. Removing all or much of the remaining gummy component from the bagworm silk thread treated with the adhesion controller can make it easy to peel the bagworm silk thread from the accumulator, and/or make it easy to peel, from one another, the bagworm silk threads cumulated on the accumulator and formed into a loop-shaped bundle, and to withdraw the silk thread.

The material for the peeling container basically follows that for the adhesion controller. The material is not limited, as long as the accumulator, the peeling container, and the inner wall thereof is neither dissolved, corroded, nor modified by the peeling solution or vapor. The material can be suitably selected in accordance with the kind of the peeling solution or vapor to be stored. For example, when high-temperature and high-pressure vapor is stored, a metal such as copper or stainless steel is preferable. Furthermore, when the peeling container stores a peeling solution composed of an aqueous solution containing a surfactant, plastics, ceramics (enamel), glass, or the like are preferable.

The peeling container can comprise a supply port for supplying a peeling solution or vapor into the peeling container, and/or a discharge port for discharging a peeling solution or vapor out of the peeling container. The peeling container can also comprise an inflow port for supplying a peeling solution into the peeling container and/or a discharge port for discharging a peeling solution out of the peeling container.

A plurality of peeling containers can be placed in one thread-producing apparatus.

The peeling solution is not limited as long as the peeling solution is a solution having the effect of washing away or removing the water-soluble gummy component of a bagworm silk thread in the same manner as the adhesion control solution. A solution comprising a component that has a stronger effect of removing the above-mentioned water-soluble gummy component than the adhesion control solution does is preferable. Examples of such a solution comprise degumming solutions to be used to degum a silkworm cocoon, such as a sodium carbonate solution, a sodium bicarbonate solution, and a Marseilles soap solution. Additionally, the vapor may be water vapor.

1-3-5. Collection Device

A "collection device" is configured to collect a bagworm silk thread peeled from the movable loop-shaped rail. In a thread-producing apparatus according to the present invention, the collection device is an optional constituent that, together with the peeling container, constitutes the collection unit, and is desirably provided to produce a long bagworm silk thread. In a thread-producing apparatus according to the present invention, the collection device is completely separated from the spinning unit.

The collection device is not limited to any structure as long as the collection device has a structure which enables the peeled bagworm silk thread to be gathered and retained. The collection device is preferably configured such that a thread collected around the periphery thereof can be reeled up. The collection device is not limited to any particular shape as long as a thread can be reeled around the periphery thereof. For example, the collection device may be in the form of any one of a disc, cylinder, rectangular column (comprising a plurality of rod members which each constitute each longitudinal edge of a rectangular column), plate, or combination thereof. A bobbin or a shape similar thereto is preferable.

Additionally, the collection device is automatically rotatably configured to reel a thread around the periphery thereof. The driving force for rotation can be, for example, an electrical power obtained via a motor or the like.

As the material of the collection device, for example, a metal, resin (comprising a synthetic resin and a natural resin), wood material (comprising a branch, bine, bamboo, and the like), ceramics, stone, or combination thereof can be utilized. The material preferably makes it possible that the portion which comes in contact with a reeled bagworm silk thread is processed into a curved face and/or a smooth face such that the thread is not damaged.

Figure 5:
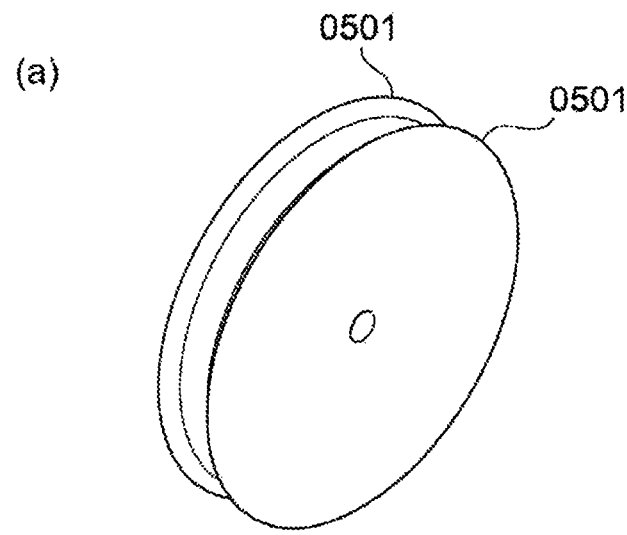
FIG. 5 shows an example of the shape of a bobbin set up on the periphery of a collection device.
Figure 5:
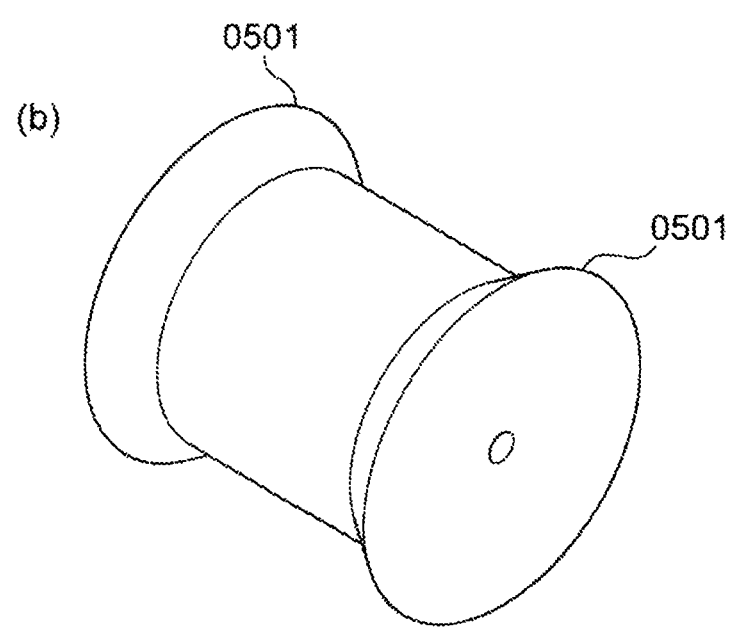

The collection device can comprise one or more concavities and convexities on the collection face of the periphery thereof. The "concavity and convexity" are configured along the longitudinal direction of the periphery of the collection device, and configured such that the collected bagworm silk thread is received in the concavity, and such that the bagworm silk thread does not fall off from the collection device. For example, when the bobbin is disc-shaped (FIG. 5(a)) or cylindrical (FIG. 5(b)), the bobbin equips salient portions (0501) at the ends, as shown in FIG. 5.

2. Method of Producing Long Bagworm Silk Thread

2-1. Overview

A second aspect of the present invention is a method of producing a long bagworm silk thread. A production method according to the present invention makes it possible that a long bagworm foothold silk thread is produced from a bagworm in an efficient manner and in a large amount without needing a special skill. Additionally, separating the spinning process group and the collecting process group eliminates the necessity of the management and regulation for the slack of reeling of the bagworm silk threads, and makes it possible to enhance the production efficiency for a long bagworm silk thread.

2-2. Method

Figure 6:
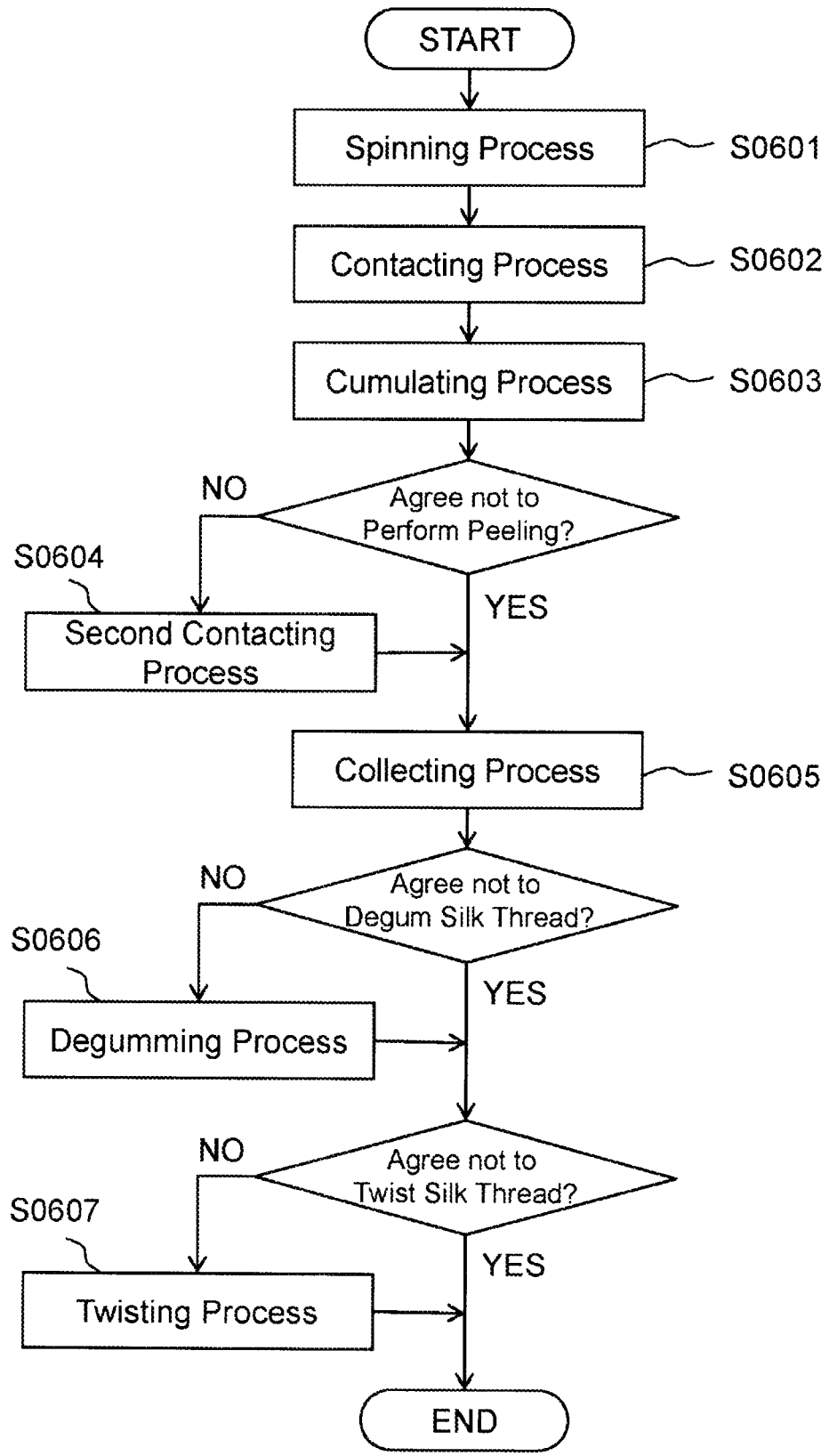
FIG. 6 is a basic process flow diagram of a method of producing a long bagworm silk thread according to the present invention.

An example of a process flow of a production method according to the present invention is shown in FIG. 6. The production method according to the present invention comprises a spinning process (S0601), a contacting process (S0602), a cumulating process (S0603), and a collecting process (S0605) as essential production processes. The method also comprises a second contacting process (S0604), a degumming process (S0606) and/or a twisting process (S0607) as optional processes. Among these, the spinning process, the contacting process, and the cumulating process are encompassed in the spinning process group related to the spinning of a bagworm silk thread, and the second contacting process, the collecting process, the degumming process, and the twisting process are encompassed in the collecting process group related to the collection and reeling of a bagworm silk thread. Each of the processes will be specifically described below.

(1) Spinning Process (S0601)

The "spinning process" is a process of making a bagworm hold its legs on a rail and continuously spin a thread in the direction along a movable loop-shaped rail under the active conditions of the bagworm. This process is encompassed in the spinning process group, and is an essential process in the production method according to the present invention.

The term "active conditions" as used herein refers to conditions under which a bagworm can perform activities involving usual movements such as migration and eating. Examples of such conditions comprise, for example, temperature, atmospheric pressure, humidity, brightness, and oxygen level, and the most important condition in the present invention is temperature. Since insects are poikilotherms, they suspend activities and enter into dormancy as the air temperature decreases. Thus, among the active conditions in the present invention, the lower limit of the preferable air temperature is a temperature at bagworm do not enter into dormancy. The specific temperature varies depending on the species, and may be generally 10° C. or more, preferably 12° C. or more, more preferably 13° C. or more, still more preferably 14° C. or more, still more preferably than 15° C. or more. On the other hand, the upper limit of the temperature is the upper limit of temperature under which a bagworm can survive. In general, the temperature may be 40° C. or less, preferably 35° C. or less, more preferably 30° C. or less, still more preferably 27° C. or less, still more preferably 25° C. or less. The atmospheric pressure, humidity, brightness, oxygen concentration, and the like may be substantially equal to, for example, those in plains in temperate areas. For example, the atmospheric pressure is around 1 atmosphere, the humidity ranges from 30 to 70%, and the brightness is maintained for 6 hours to 18 hours out of 24 hours, and the concentration of oxygen in the atmosphere ranges from 15 to 25%.

A bagworm used in this process may be a bagworm collected in the field or alternatively a bagworm bred in successive generations under artificial conditions. Preferably, neither of the bagworms is fasted, and more preferably, either is fed much before use. If a bag worm used in this process is not starved but is fed sufficiently, the bagworm continuously spins a thread with moving on a rail under the above-described conditions for a period from 1 hour to 4 days, from 3 hours to 3 days, or from 6 hours to 2 days.

A bagworm used in this process may be having a nest or may be left out of a nest. Since a bagworm generally behave with a nest, the bagworm in a nest is suitably used in this process. For example, however, when a bagworm is used in the present process with a tubular fixator in which the naked bagworm taken out of a nest is received, the bagworm does not need to hold a nest. When a bagworm holds a nest, the nest does not need to be intact, as long as the nest can hide almost the whole body of the bagworm. The nest is not necessarily composed of natural materials such as pieces of leaves and twigs and may be created using artificial materials (such as paper pieces, wood chips, discrete fibers, metal pieces, plastic pieces, and the like).

The present process is characterized in that a bagworm is fixed at a position at which the legs of the bagworm can hold the rail. This fixation restricts the free movement of the bagworm, thus making it possible to fix the spinning direction on the rail to a given direction. In this regard, one bagworm is placed and fixed on one rail in principle, but a plurality of bagworms can be fixed on one rail. In this case, the bagworms are placed and fixed on a rail in such a manner that the bagworms move in the same direction.

The constitution and structure of a rail to be used for a production method according to the present invention may comply with a constitution and structure of the rail in the apparatus for producing a bagworm silk thread as described in the first aspect. The structure is preferably a loop-shaped rail, especially a circular loop-shaped rail. A plurality of rails may be used. In this case, the rails may be placed in parallel so that each bagworm can be fixed in such a manner that the legs of each bagworm hold each rail. The bagworm is fixed using a fixator or the like. The fixator may be constituted as described in the first aspect. Once a bagworm is allowed to hold a rail under the active conditions, the bagworm will continuously spin a thread while spontaneously moving along the rail.

The phrase "continuously spin a thread" as used herein refers to a bagworm's spinning a thread without interruption. A bagworm holding a rail with the legs continues to spin a foothold silk thread by instinctive nature while moving. Once spinning a silk thread spewed from the right and left spinnerets located on the mouth of a larva breaks, the continuity is lost.

In this process, the direction in which a bagworm with the legs holding a rail moves, is the direction of movement of the bagworm in principle. As above-mentioned, a bagworm used in the present process is fixed at a position at which the legs of a bagworm are holding a rail. In this state, the bagworm cannot move in any direction other than the direction of movement. When a bagworm moves reverse on a rail uncommonly, a ratchet equipped on the rail restricts such a reverse movement on the rail, and thus, the direction of movement inevitably results only in the direction of advance.

Another characteristic of the present process is that the rail is moved in the longitudinal direction automatically and/or by the movement of a bagworm. This makes it possible that a bagworm continuously spins on a rail even though fixed at given position.

The rail is moved by the movement impelling force of a bagworm moving with holding the rail with the legs. Accordingly, the direction of movement of the rail is opposite to the direction of movement of a bagworm. When the rail is a circular loop-shaped rail constituted around the marginal portion of a disc, the rail can move by rotating the disc by the movement of a bagworm. The rail may be moved automatically. In this case, the direction of movement of the rail is opposite to the direction of movement of a bagworm.

When the moving speed of a rail is based on the movement impelling force of a bagworm, it is substantially equal to the moving speed of the bagworm. Also when the rail is moved automatically, the moving speed of the rail is adjusted so as to be approximately equal to or less than the moving speed of a bagworm. When the rail is moved automatically, the rail can be moved using a known driving technique, for example, a combination of a motor and a gear. As above-mentioned, the usual moving speed of a bagworm is in the range of from 3 m/hr to 15 m/hr, or in the highest range of from 17 m/hr to 22 m/hr. Accordingly, when the rail is moved automatically, a speed (v) may be equal to or less than these speeds. For example, the moving speed is in the following ranges: $0 \text{ m/hr} < v \leq 22 \text{ m/hr}$, $0 \text{ m/hr} < v \leq 20 \text{ m/hr}$, $0 \text{ m/hr} < v \leq 17 \text{ m/hr}$, $0 \text{ m/hr} < v \leq 15 \text{ m/hr}$, $0 \text{ m/hr} < v \leq 12 \text{ m/hr}$, $0 \text{ m/hr} < v \leq 10 \text{ m/hr}$, $0 \text{ m/hr} < v \leq 8 \text{ m/hr}$, $0 \text{ m/hr} < v \leq 5 \text{ m/hr}$, $0 \text{ m/hr} < v \leq 4 \text{ m/hr}$, or $0 \text{ m/hr} < v \leq 3 \text{ m/hr}$.

Since a method according to the present invention enables a bagworm to continue to spin a silk thread on a movable loop-shaped rail, a long bagworm foothold silk thread can be produced.

(2) Contacting Process (S0602)

The "contacting process" is a process in which a bagworm silk thread on the movable loop-shaped rail is brought in contact with an adhesion control solution. This process is encompassed in the spinning process group, and is an essential process in the production method according to the present invention. This process washes away or removes a part of a gummy component holding a bagworm silk thread bonded onto the rail, and reduces the adhesive force of the gummy component. This results in weakening the adhesion of the bagworm silk thread to the rail and the adhesion between the bagworm silk threads due to the cumulation of the bagworm silk threads, and thus, the bagworm silk thread becomes adhesive and also capable of being easily peeled.

This process is preferably performed at an early stage after the spinning process is performed and before the gummy component on the surface of the bagworm silk thread is dried and solidified. Preferably, the process is performed immediately after the spinning process. Accordingly, this process is performed substantially concurrently in conformity with the spinning process as long as the bagworm keeps spinning on the movable loop-shaped rail continuously.

An adhesion control solution to be used in this process is the same as the adhesion control solution described in the first aspect. A method of bringing the adhesion control solution in contact with a bagworm silk thread spun on a rail is not limited. For example, a part of the rail after the spinning process may be immersed in the adhesion control solution stored in a vessel, or the adhesion control solution may be dripped, sprayed, scattered, or applied to the bagworm silk thread spun on the rail after the spinning process. Alternatively, the adhesion control solution may be exuded through a groove or a hole provided in the rail. Alternatively, such methods may be combined.

In a method of producing a long bagworm silk thread according to the present invention, a movable loop-shaped rail is used. Thus, this contacting process is performed immediately after the bagworm silk thread is spun on the rail in the spinning process, and the circling of the movable loop-shaped rail makes it possible that the bagworm silk thread which has once undergone this process can undergo this process again.

(3) Cumulating Process (S0603)

The "cumulating process" is a process of accumulating the bagworm silk threads after the contacting process. This process, together with the spinning process and the contacting process, is encompassed in the spinning process group, and is an essential process in the production method according to the present invention.

A place at which the bagworm silk threads are cumulated is not limited. In cases where the spinning process is performed in such a manner that a bagworm fixed with a fixator is allowed to spin on a movable loop-shaped rail, the bagworm silk threads are cumulated on an accumulator on the movable loop-shaped rail.

The cumulating process is performed after the movable loop-shaped rail has circled from the starting point at which the spinning process started. In a method of producing a long bagworm silk thread according to the present invention, the bagworm silk thread spun is not collected immediately but collected after the spinning process is completed. Because of this, the bagworm silk threads spun on the movable loop-shaped rail in the spinning process continues to be cumulated through the circling of the rail all the time until the spinning process is completed. Accordingly, this process is continued as long as the spinning process is continued.

In this regard, the completion of the spinning process is followed by the completion of the contacting process and the cumulating process, and thus, the spinning process group ends. The spinning process group is performed independently from the collecting process group, and thus, the collecting process group can be performed immediately after the spinning process group ends, or the collecting process group can be performed with some time between both of the process groups.

(4) Second Contacting Process (S0604)

The "second contacting process" is a process of bringing the cumulated bagworm silk thread in contact with a peeling solution and/or vapor after the cumulating process. This process is encompassed in the collecting process group, and is an optional process in the method of producing a long bagworm silk thread according to the present invention. Performing this process after the cumulating process and before the collecting process makes it possible that the bagworm silk threads cumulated are prevented from adhering again via the gummy component not completely removed in the contacting process, and that the bagworm silk threads, even if allowed to adhere again, are easily collected again from the rail.

This process is typically performed after the cumulating process and before the below-mentioned collecting process, or can be performed concurrently with the collecting process.

A peeling solution and vapor to be used in this process follows the peeling solution and vapor described in the first aspect. A method of bringing a peeling solution and/or vapor in contact with bagworm silk threads cumulated on a rail is not limited. Examples of such methods comprise: a method in which the whole or a part of the rail after the cumulating process is immersed in a peeling solution contained in a tank; a method in which the whole or a part of the rail after the cumulating process is brought in contact with water vapor filled in a tank; a method in which a peeling solution is dripped, sprayed, scattered, or applied to bagworm silk threads cumulated on the rail after the cumulating process; a method in which water vapor is sprayed onto bagworm silk threads cumulated on the rail after the cumulating process; and combinations of these methods.

Additionally, using a degumming solution as a peeling solution makes it possible that the second contacting process doubles as the degumming process (S0606) as described below. In this case, the subsequent collecting process can collect a monofiber formed by separating a bifilament, not spun fiber. The degumming process will be described later.

(5) Collecting Process (S0605)

The "collecting process" is a process of peeling and collecting a cumulated bagworm silk thread after the cumulating process. This process is encompassed in the collecting process group, and is an essential process in the method of producing a long bagworm silk thread according to the present invention. The bagworm silk thread after the contacting process or the second contacting process has the gummy component removed or decreased, and thus, is easier to peel from the rail and the same bagworm silk thread. Accordingly, peeling an end of a bagworm silk thread from the rail, followed by applying tension in the direction opposite to the direction in which the bagworm silk thread is reeled on the loop-shaped rail, makes it possible to easily peel the bagworm silk threads cumulated on the rail.

A method of collecting bagworm silk threads cumulated on the rail is not limited as long as the method does not make the bagworm silk thread be torn. In a production method according to the present invention, a method in which a thread is reeled on a bobbin to be collected is preferable. A usual bobbin used in the art can be used. For example, the thread can be reeled around the periphery of a disc-shaped member, tubular member, plate-like member, or the like.

In a specific example of collection, fixing, on a bobbin, an end of a bagworm silk thread on the movable loop-shaped rail, and rotating the bobbin with tension applied in the direction opposite to the direction in which the bagworm silk threads cumulated on the accumulator is reeled makes it possible to collect, around the bobbin, the bagworm silk threads on the accumulator. During this, the movable loop-shaped rail needs only to be rotated in synchronism with the rotation of the bobbin. This allows a degree of tension to be always applied to the bagworm silk thread between the rail and the bobbin, thus making it possible to prevent slack of reeling.

The rotation speed of the bobbin is not limited. However, too high a rotation speed causes the tension applied to the bagworm silk thread between the rail and the bobbin to be too strong, and as a result, creates the possibility that the bagworm silk thread is torn. Because of this, the rotation speed of the bobbin may be in the range of 15 m/hr or less or 22 m/hr or less. For example, the suitable rotation speed is in the following ranges: $0\ \text{m/hr} < v \leq 22\ \text{m/hr}$, $0\ \text{m/hr} < v \leq 20\ \text{m/hr}$, $0\ \text{m/hr} < v \leq 17\ \text{m/hr}$, $0\ \text{m/hr} < v \leq 15\ \text{m/hr}$, $0\ \text{m/hr} < v \leq 12\ \text{m/hr}$, $0\ \text{m/hr} < v \leq 10\ \text{m/hr}$, $0\ \text{m/hr} < v \leq 8\ \text{m/hr}$, $0\ \text{m/hr} < v \leq 5\ \text{m/hr}$, $0\ \text{m/hr} < v \leq 4\ \text{m/hr}$, or $0\ \text{m/hr} < v \leq 3\ \text{m/hr}$. When the bobbin is moved automatically, the rail can be moved using a known driving technique, for example, a combination of a motor and a gear.

(6) Degumming Process (S0606)

The "degumming process" is a process of degumming a long bagworm silk thread. The term "degumming" refers to removing a sericin-like gummy component from a spun fiber to obtain a monofiber. This process is typically performed after the above-mentioned collecting process, and may be performed concurrently as the second contacting process, as above-mentioned. Additionally, when the twisting process is performed before this process and after the collecting process, as described below, this process may be performed after the twisting process. This process is an optional process and may be performed if necessary.

A method of degumming a bagworm silk thread is not limited as long as a gummy component can be removed without weakening the strength of a fiber component of the silk thread. For example, a method of degumming a silkworm silk thread can be applied. Specifically, a bagworm silk thread collected in the collecting process is immersed in a degumming solution such as a solution having a sodium bicarbonate concentration of 0.01 mol/L to 0.1 mol/L, 0.03 mol/L to 0.08 mol/L, or 0.04 mol/L to 0.06 mol/L. More preferably, the thread is boiled for a time period from 5 minutes to 1 hour, 10 to 40 minutes, or 15 to 30 minutes. This process makes it possible to obtain a monofiber from a long foothold silk thread.

(7) Twisting Process (S0607)

The "twisting process" is a process of twisting a bagworm silk thread obtained after the collecting process or the degumming process. The term "twisting" refers to winding threads together to produce a yarn. In this process, a plurality of bagworm silk spun fibers and/or monofibers are twisted to produce a bagworm silk thread having toughness.

In the twisting process, monofibers from bagworm silk threads obtained after the degumming process may be gathered into a bundle and then twisted, or alternatively bagworm silk spun fibers obtained after the collecting process may be gathered into a bundle and then twisted. In the former case, a twisted bagworm silk yarn without a gummy component is obtained. In the latter case, a twisted bagworm silk yarn consisting of spun fibers and having the remaining gummy component is obtained. Thus, the obtained bagworm silk yarn may be used as a bagworm silk yarn which has not undergone the degumming process and consequently encompasses a gummy component, or may be degummed as necessary to produce a twisted bagworm silk yarn from without a gummy component.

In this process, a bagworm silk thread may be blended with another fiber, for example, an animal fiber such as a silkworm silk thread, a plant fiber such as a cotton fiber, a synthetic fiber such as a polyester fiber, or a recycled fiber such as rayon, or the like, to form a bundle of fibers, which is in turn twisted. In the production of one strand of twisted bagworm silk yarn, the number of constituent spun fibers and/or monofibers is not limited to a particular number. For example, the number ranges from 2 to 200, from 4 to 150, from 6 to 100, from 8 to 50, or from 10 to 30.

The twisting is not limited to any particular method. Any twisting method known in the art may be implemented. Examples of the methods comprise right-laid (S-laid) and left-laid (Z-laid). The twist number may be determined as appropriate. Plural strands of twisted bagworm silk yarn may be further twisted together by a process called plying to produce a thicker bagworm silk yarn. The twisting operation may be performed by hand or by using a yarn twister.

A long bagworm silk thread, which is obtained by a production method according to the present invention, can be spun together into a longer bagworm silk yarn.

A long bagworm silk thread, which has hitherto been considered impossible to produce, can be produced as a monofiber or a fiber assembly thorough the above-mentioned processes. Accordingly, a fabric comprising a bagworm foothold silk thread, which has hitherto been impossible to produce, can also be produced using a long bagworm silk thread according to the present invention as a sole material or in combination with another fiber. A fabric made of a bagworm silk thread is beautiful and smooth, has excellent tensile strength. Thus, a long bagworm silk thread is promising not only as a material for clothes but also as a special material for, for example, medical materials and protective clothes, as in the case of a spider thread. The Long bagworm silk thread can further be used for quality fabric products, for example, quality legless chairs, sofas, curtains, fabric wallpapers, and the like, to which strong friction force is often applied.

EXAMPLES

<Fabrication of Apparatus for Producing Bagworm Silk Thread, and Verification of Length of Produced Thread>
(Purpose)

An apparatus for producing a bagworm silk thread according to the present invention is fabricated to verify the following: that a bagworm silk thread is not reeled slackly during the operation of the apparatus; and that the production output of the bagworm silk thread that can be produced per day is larger than that apparatus for producing a bagworm silk thread which is disclosed in the Examples section in JP2018-227669.
(Method)
1. Fabrication of Apparatus In this Example, an apparatus for producing a bagworm silk thread as described in the first aspect of the present invention was fabricated.

The movable loop-shaped rail was a circular movable loop-shaped rail constituted around the periphery of a disc having a diameter of 12 cm and a thickness of 2.1 mm. This movable loop-shaped rail can be rotated around the central axis of the disc.

A polypropylene-made centrifuge tube having a diameter of 18 mm (having an inner diameter of 16 mm) was used for the fixator; this centrifuge tube was slanted at an angle of approximately 30 degrees with respect to the horizontal plane; and the legs of a bagworm fixed to the fixator were allowed to hold the upper portion of the movable loop-shaped rail.

A storage tank storing 1 L of an adhesion control solution of 0.1% polyethylene glycol stearate (n=approximately 40, from Tokyo Chemical Industry Co., Ltd., Cas. No. 9004-99-3) was used as an adhesion controller. The movable loop-shaped rail was placed vertically in the apparatus (in such a manner that the disc face is perpendicular to the horizontal face), and the lower portion of the disc was configured so as to be immersed in the adhesion control solution in the storage tank.

The collection device was a bobbin having an internal diameter of 0.9 cm.
2. Production of Long Bagworm Silk Thread
(1) Material As bagworms, the last instar larvae of *Eumeta japonica* were used.
(2) Method of Producing Half of the bagworm together with a nest was inserted and fixed in a centrifuge tube as a fixator. Subsequently, the legs of the bagworm were allowed to hold the movable loop-shaped rail placed vertically. The rail was adjusted so that the rail might be rotated in the direction opposite to the direction of movement of the bagworm as the bagworm migrated forward. The bagworm silk thread spun on the rail was immediately immersed in the adhesion control solution in the adhesion controller placed around the lower portion of the rail, and then treated with the adhesion control solution a plurality of times every time the rail was circled. The bagworm was allowed to spin on the rail continuously for approximately 5 hours.

After completion of the spinning, the bagworm was removed from the fixator, and an end of the bagworm silk threads cumulated on the accumulator on the movable loop-shaped rail was taken up and connected with the collection device. Subsequently, the collection device was rotated in such a manner that tension was applied to the bagworm silk thread in the direction opposite to the direction in which the bagworm silk thread was reeled around the accumulator, so that the bagworm silk thread was reeled and collected around the collection device from the accumulator. Then, the length of the bagworm silk thread reeled was measured.

As a control, a thread-producing apparatus disclosed in the Examples section in JP2018-227669 (hereinafter referred to as a "prior application device") was used. A bagworm was allowed to spin on a rail continuously for approximately 5 hours in accordance with the production method disclosed in the Examples section in JP2018-227669 (hereinafter referred to as a "prior application method"). The processes after the spinning were performed in accordance with the above-mentioned methods.

RESULTS

The length of the bagworm silk thread obtained with the prior application device was 269.7 m, whereas the length of the bagworm silk thread obtained with the thread-producing apparatus according to the present invention was 636.2 m, that is, more than two times as long. Additionally, in a thread-producing space having the same size, 10 prior application devices were enabled to be placed, whereas 20 or more thread-producing apparatuses according to the present invention were enabled to be placed. Furthermore, slack of reeling often occurred between the rail and the collection device in the prior application device during thread-producing, but did not occur in the thread-producing apparatus according to the present invention.

The above-mentioned results have revealed that, compared with the prior application device, a thread-producing apparatus according to the present invention enables the thread-producing amount per predetermined time to increase by two times or more, and makes it possible to decrease the thread-producing space by approximately 50%, thus making it possible to enhance the production efficiency markedly.

Additionally, the results have revealed that the thread-producing apparatus according to the present invention eliminates the necessity of a supervisor who monitors and obviates the slack of reeling of the bagworm silk thread during thread-production, and thus, the apparatus leads to a reduction in necessary labor costs.

All publications, patents, and patent applications cited herein should be incorporated herein by reference in their entirety.

The invention claimed is:

1. An apparatus for producing a bagworm silk thread, comprising: a movable loop-shaped rail comprising an accumulator; a fixator configured to fix a bagworm; and an adhesion controller;
   wherein the movable loop-shaped rail has a width smaller than the maximum width between the right and left legs of the bagworm fixed with the fixator, and is configured to be held by the legs of the bagworm,
   wherein the accumulator is integrally placed on the movable loop-shaped rail, and configured such that the bagworm silk thread spun on the movable loop-shaped rail by the bagworm fixed with the fixator can be cumulated,
   wherein the fixator is placed at a position such that the bagworm fixed can hold the movable loop-shaped rail, and
   wherein the adhesion controller stores an adhesion control solution, and is configured such that the bagworm silk thread spun on the movable loop-shaped rail is brought in contact with the adhesion control solution,
   the apparatus further comprising one or more peeling containers,
   wherein the peeling container is configured to store a peeling solution and/or vapor for peeling the bagworm silk thread from the accumulator, and placed at a position such that the whole or a part of the accumulator can be brought in contact with the peeling solution and/or the vapor in the peeling container.

2. The apparatus for producing a bagworm silk thread according to claim 1, further comprising a collection device independent from the movable loop-shaped rail, wherein the collection device is configured to collect the bagworm silk thread from the accumulator.

3. The apparatus for producing a bagworm silk thread according to claim 1, wherein the movable loop-shaped rail is circular.

4. The apparatus for producing a bagworm silk thread according to claim 1, wherein the movable loop-shaped rail is an automatic rail.

5. The apparatus for producing a bagworm silk thread according to claim 2, wherein the collection device comprises, on the periphery thereof, a bobbin configured to reel the bagworm silk thread.

6. A method of producing a long bagworm silk thread, comprising:
   a spinning process of making a bagworm hold a movable loop-shaped rail with its legs and continuously spin along the movable loop-shaped rail,
   wherein the movable loop-shaped rail has a width smaller than the maximum width between the right and left legs of the bagworm used for thread-production, and is configured such that the legs of the bagworm can hold the movable loop-shaped rail;
   a contacting process of bringing the bagworm silk thread on the movable loop shaped rail in contact with an adhesion control solution after the spinning process;
   a cumulating process of accumulating the bagworm silk thread after the contacting process; and
   a collecting process of collecting the cumulated bagworm silk thread after the cumulating process;
   wherein in the spinning process, the bagworm for use or a bagworm nest thereof is fixed at a position such that the legs of the bagworm can hold the movable loop-shaped rail, and wherein the movable loop-shaped rail is configured to be moved in the longitudinal direction automatically and/or by the movement of the bagworm.

7. The production method according to claim 6, further comprising a second contacting process of bringing the bagworm silk thread cumulated on the rail after the cumulating process in contact with a peeling solution and/or vapor.

* * * * *